United States Patent
Schomaker et al.

(10) Patent No.: US 12,258,541 B2
(45) Date of Patent: Mar. 25, 2025

(54) CRUMBLY PHASE COMPOSITION OF METHYLGLYCINE N,N DIACETIC ACID

(71) Applicant: NOURYON CHEMICALS INTERNATIONAL B.V., Arnhem (NL)

(72) Inventors: Elwin Schomaker, Deventer (NL); Paulus Johannes Cornelis Van Haeren, Deventer (NL); Martin Heus, Deventer (NL); Marco Ypma, Deventer (NL); Stijn Richard Gerard Oudenhoven, Deventer (NL); Roy Gérard Doppen, Deventer (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 623 days.

(21) Appl. No.: 17/415,786

(22) PCT Filed: Dec. 17, 2019

(86) PCT No.: PCT/EP2019/085755
§ 371 (c)(1),
(2) Date: Jun. 18, 2021

(87) PCT Pub. No.: WO2020/127349
PCT Pub. Date: Jun. 25, 2020

(65) Prior Publication Data
US 2022/0073842 A1 Mar. 10, 2022

(30) Foreign Application Priority Data
Dec. 21, 2018 (EP) .................................. 18215420

(51) Int. Cl.
| | | |
|---|---|---|
| *C11D 3/26* | (2006.01) | |
| *C07C 229/16* | (2006.01) | |
| *C11D 3/30* | (2006.01) | |
| *C11D 3/33* | (2006.01) | |
| *C11D 7/32* | (2006.01) | |
| *C11D 11/02* | (2006.01) | |
| *C11D 17/00* | (2006.01) | |
| *C11D 17/06* | (2006.01) | |

(52) U.S. Cl.
CPC .............. *C11D 3/33* (2013.01); *C07C 229/16* (2013.01); *C11D 3/30* (2013.01); *C11D 7/3245* (2013.01); *C11D 11/02* (2013.01); *C11D 17/06* (2013.01); *C11D 17/065* (2013.01); *C07B 2200/13* (2013.01); *C11D 2111/14* (2024.01)

(58) Field of Classification Search
CPC ........... C11D 3/30; C11D 3/33; C11D 7/3245; C11D 17/06; C11D 17/065
USPC .................................. 510/480, 499, 444, 445
See application file for complete search history.

(56) References Cited

U.S. PATENT DOCUMENTS

| | | |
|---|---|---|
| 5,981,798 A | 11/1999 | Schoenherr et al. |
| 8,628,684 B2 | 1/2014 | Mrzena et al. |
| 9,376,649 B2 | 6/2016 | Baranyai |
| 9,751,829 B2 | 9/2017 | Baranyai |
| 2009/0018094 A1 | 1/2009 | Stolte et al. |
| 2012/0046491 A1 | 2/2012 | Mrzena et al. |
| 2012/0149936 A1 | 6/2012 | Baranyai |
| 2014/0073554 A1 | 3/2014 | Van Der Eerden et al. |
| 2014/0155646 A1 | 6/2014 | Mrzena et al. |
| 2016/0221930 A1 | 8/2016 | Baranyai |
| 2018/0355285 A1 | 12/2018 | Jaekel et al. |
| 2020/0181537 A1 | 6/2020 | Reinoso et al. |

FOREIGN PATENT DOCUMENTS

| | | | |
|---|---|---|---|
| CN | 103649017 A | 3/2014 | |
| CN | 110312785 A | 10/2019 | |
| CN | 110869345 A | 3/2020 | |
| EP | 0 845 456 A2 | 6/1998 | |
| EP | 2392638 A1 | 12/2011 | |
| JP | 2007532753 A | 11/2007 | |
| JP | 2013253118 A | 12/2013 | |
| JP | 2016534138 A | 11/2016 | |
| JP | 2017522168 A | 8/2017 | |
| JP | 2020526510 A | 8/2020 | |
| JP | 2022515764 A | 2/2022 | |
| WO | 2009/103882 A1 | 8/2009 | |
| WO | 2010/133618 A1 | 11/2010 | |
| WO | 2011/023382 A2 | 3/2011 | |
| WO | 2012/1500155 A1 | 11/2012 | |
| WO | 2012/168739 A1 | 12/2012 | |
| WO | 2015/173157 A1 | 11/2015 | |
| WO | WO-2016058875 A1 * | 4/2016 | .......... C07C 227/26 |
| WO | WO-2016142228 A1 * | 9/2016 | .......... C07C 227/18 |
| WO | 2017/102483 A1 | 6/2017 | |
| WO | WO-2017097657 A1 * | 6/2017 | .......... C07C 227/40 |
| WO | WO-2017174413 A1 * | 10/2017 | .......... C07C 227/26 |
| WO | WO-2018011027 A1 * | 1/2018 | .......... C07C 227/36 |
| WO | 2018/15876 A1 | 8/2018 | |
| WO | 2018153876 A1 | 8/2018 | |
| WO | WO-2019007943 A1 * | 1/2019 | .......... C07C 227/00 |
| WO | WO-2019007944 A1 * | 1/2019 | .......... C07C 227/42 |
| WO | WO-2019228849 A1 * | 12/2019 | .......... C07C 227/42 |
| WO | 2020064379 A1 | 4/2020 | |
| WO | WO-2020094480 A1 * | 5/2020 | |
| WO | 2020127349 A1 | 6/2020 | |

* cited by examiner

*Primary Examiner* — Gregory R Delcotto
(74) *Attorney, Agent, or Firm* — LKGLOBAL | Lorenz & Kopf, LLP

(57) ABSTRACT

The present invention relates to a crumbly phase composition containing on total weight of the composition
(i) 70-87 wt % of organic compounds and salts thereof containing 85 to 100 wt % on total organic compounds and salts thereof of MGDA-Na3, wherein at least 60 wt % of the MGDA-Na3 is crystalline, and
(ii) 13-30 wt % of water
The invention furthermore relates to a process to prepare the above composition and a process to prepare crystals of MGDA-Na3 by drying the above composition.

18 Claims, No Drawings

CRUMBLY PHASE COMPOSITION OF METHYLGLYCINE N,N DIACETIC ACID

This application is a 371 of PCT/EP2019/085755 filed Dec. 17, 2019, which claims foreign priority benefit under 35 U.S.C. § 119 of European Patent Application No. 18215420.3, filed Dec. 21, 2018, the disclosures of which are incorporated herein by reference.

The present invention relates to a crumbly phase composition of MGDA-Na3, the trisodium salt of methylglycine N,N diacetic acid, a process to prepare such crumbly phase composition and a process wherein this crumbly phase composition is dried to give crystalline MGDA-Na3 product.

MGDA-Na3, the trisodium salt of methylglycine-N, N-diacetic acid, is a known chelating agent having a good biodegradability, and is employed in several applications. Many of these applications involve the use of solid, preferably granular, MGDA-Na3. For example, when formulating solid detergent compositions such as powdery or tableted dishwashing formulations it is important that the MGDA-Na3 component is available in a dry and solid form.

Preparing a solid of MGDA-Na3 is not always straightforward. Storing a MGDA-Na3 solid similarly also has its challenges. If the solid MGDA-Na3 is mainly amorphous it will be quite hygroscopic, and hence sensitive to storage at humid conditions, in which case the material absorbs water, yielding a tacky material which makes the solid less suitable for use in solid formulations as these solids quickly lose their free-flowing properties.

The hygroscopicity of solid MGDA-Na 3 was found to be lower when the MGDA-Na3 is present in (primarily the) crystalline form. When isolated as a crystal instead of as an amorphous solid, the free-flowing properties of MGDA are also improved. Some varieties of crystalline MGDA-Na3 (the trisodium salt of methyl glycine-N,N-diacetic acid) are known in the art, recognizable via XRD-analysis, yielding different characteristic diffraction patterns.

Today three crystalline modifications are known for MGDA-Na3.

WO2012/168739 discloses a process of spray drying MGDA-Na3 starting from a slurry, next agglomerating the obtained solid and subsequently comminuting the obtained agglomerate. The document says that using this process more of the crystalline dihydrate is obtained over the less desired monohydrate. The dihydrate crystal in this document will be referred to as crystal type I and what is called the monohydrate is referred to as crystal type II.

WO2019/007944 discloses a third crystal type, called crystal type III.

The crystal types I, II and III can be defined by the below diffraction patterns as given in Table 1.

TABLE 1

| Crystal Type I, II and III diffraction patterns | | | | | |
|---|---|---|---|---|---|
| type I | | type II | | Type III | |
| 2Θ | d (Å) | 2Θ | d (Å) | 2Θ | d (Å) |
| 8.2 | 10.8 | 8.4 | 10.5 | 5.8 | 15.2 |
| 10.5 | 8.4 | 9.5 | 9.3 | 7.5 | 11.8 |
| 15.6 | 5.7 | 11.1 | 8 | 8.1 | 10.9 |
| 16.5 | 5.4 | 13.2 | 6.7 | 9.5 | 9.3 |
| 17.1 | 5.2 | 13.9 | 6.4 | 11.7 | 7.6 |
| 18.1 | 4.9 | 15.8 | 5.6 | 13.9 | 6.4 |
| 18.8 | 4.7 | 16.5 | 5.35 | 15.1 | 5.9 |
| 21 | 4.25 | 16.8 | 5.25 | 16.5 | 5.4 |
| 21.4 | 4.15 | 17.3 | 5.1 | 17.3 | 5.1 |
| 22.6 | 3.9 | 17.7 | 5 | 18.5 | 4.8 |
| 23.7 | 3.75 | 18.9 | 4.7 | 19.1 | 4.65 |
| 24.7 | 3.6 | 20.3 | 4.35 | 20.1 | 4.4 |

In WO2012/168739 it is shown that for many applications crystal type I is the preferred variety, as it is less hygroscopic than crystal type II. Powders or granules containing a high degree of crystal type I keep their free-flowing character better upon storage at high humidity conditions, while products containing only or mainly the type II variety fail at these conditions.

Processes to prepare crystalline MGDA-Na3 are however not leading to a high yield or good quality of product and/or involve quite some steps, a high energy consumption and/or waste streams.

WO 2010/133618 discloses a process of concentrating an aqueous solution of MGDA-Na3 (20-60 wt %) in an evaporator with rotating internals yielding a crystal slurry having a solid concentration in the range from 60 to 85 wt %, which is subsequently aged in a paste bunker and then dosed to a thin-film contact dryer. Two different crystal varieties or mixtures of these can be obtained by this process, referred to as crystal modification 1 and 2, corresponding to types II and I respectively in table 1. Even though WO 2010/133618 specifies the solid concentration to be 60 to 85 wt % it also clearly states that this composition is a slurry. The Examples of WO 2010/133618 do not go higher than slurries containing 69% wt % of solids, which are cooled while stirring, from which it must be concluded that one still deals with a liquid dispersion, and not a crumbly phase composition. The process of WO 2010/133618 is rather sensitive towards concentration fluctuations as in the concentration ranges as mentioned in the examples, MGDA-Na3 behaves as a thixotropic paste, which rheological properties are highly dependent on concentration, seriously raising the chance on fouling, in case of process parameter fluctuations, up to full blockage of the process line.

WO2018/153876 discloses a process to crystallize MGDA alkali metal salts in the presence of a particulate solid with a specific pore volume such as ground alumina, ground molecular sieves or silica powder in an amount of 0.1-2.0 wt % on the basis of a 35-60 wt % MGDA alkali metal salt solution. The process leads to solid MGDA alkali metal products with high crystallinity that contain at least 90 wt % of crystal type I and at least 1 wt % of crystal type II, and that contain inherently a particulate solid contamination.

WO 2015/173157 discloses a process to crystallize chelating agents from a dispersion wherein the dispersion is milled. In the Examples also MGDA-Na3 is crystallized employing the above process. In the Example wherein MGDA-Na3 is crystallized, to a dispersion that contains 50 wt % of MGDA-Na3, 20 wt % of MGDA-Na3 seeds are added, to give a dispersion hence containing 58 wt % of MGDA-Na3. Following the above process, a product is obtained that has a crystallinity of 67% when milling is employed and 60% when in comparison no milling is employed. The process is further characterized in that it concerns the presence of a considerable amount of water.

WO2011/023382 and WO2009/103822 disclose processes for preparing MGDA-Na3 by spray granulating an aqueous solution or slurry of MGDA-Na3. Important disadvantages of such processes is that the energy consumption of such process is high and that equipment for spray granulation requires quite a lot of factory space. Moreover, using these processes, it is very difficult up to impossible to obtain a product having a high crystallinity, in particular when one aims after obtaining a product containing for example only the favored type I crystalline variety.

WO2017/102483 discloses a process to crystallize MGDA-Na3 by salting out. Such a process will lead to a product that is contaminated with salt impurities, unless the product is washed extensively, yielding a waste stream.

A general disadvantage of crystallization processes in which the crystals are harvested, which also holds for WO2012/150155 disclosing a seeded evaporative crystallization process of L-MGDA-Na3 or WO2015/173157, is that one ends up with a mother liquor, in which the byproducts of the MGDA-Na3 production process are concentrated, eventually yielding a waste stream. Also, crystallization processes for drying MGDA-Na3 usually involve the circulation of considerable amounts of water as a solvent or as a mother liquor, or when the mother liquor is disposed of, the creating of considerable waste streams.

The present invention aims to provide an improved process to prepare solid crystalline MGDA-Na3 that does not have the above disadvantages. The invention is based on a new form of MGDA-Na3, called the crumbly phase, in which there is limited water and the MGDA-Na3 is present in a crystalline state for the major part so that a non-pasty, crumble like texture is obtained. When such crumbly phase is used as a feed for a drying process, one obtains an efficient process characterized by a high yield of high-quality product, in which circulating water can be limited, and waste streams can be avoided.

The present invention hence provides a crumbly phase composition containing on total weight of the composition
(i) 70-87 wt % of organic compounds and salts thereof wherein 85 to 100 wt % on total organic compounds and salts thereof is MGDA-Na3 and at least 60 wt % of the MGDA-Na3 is crystalline, and
(ii) 13-30 wt % of water.

The crumbly phase is a phase comprising weakly agglomerated particulate solids covered with a thin layer of a MGDA-Na3 composition, showing a rheological behavior that resembles or at least approaches the behavior of dry particulate material. The thin layer of the MGDA-Na3 composition is preferably a (saturated) aqueous solution of MGDA-Na3.

It should be noted that though the crumbly phase product is defined as having an organic compounds and salts content and a water content, this is not intended to mean that the water is fully present as a separate liquid water phase. Part of the water can be present as crystal water and thereby can be seen as solid-state water. In the crumbly phase composition as covered by the present invention the water is defined to cover both free water and crystal water. The amount of water can be determined by Karl-Fischer titration.

Crumbly phase behavior has the advantage compared to a thixotropic paste of much easier handling and was found to be much easier dried into free-flowing granules.

Organic compounds are compounds that have a hydrocarbon backbone wherein this hydrocarbon backbone may contain one or more heteroatoms like oxygen or nitrogen atoms. The group of organic compounds includes organic acids and bases such as carboxylic acids. If carboxylic acids are present in the organic compounds fraction, the salts of such carboxylic acids are also seen as part of the organic compounds fraction in this document. Crystal water is not included in the weight fraction of the organic compounds, and neither are inorganic compounds such as inorganic salts.

The invention in addition provides a process to prepare the above crumbly phase composition by combining an aqueous composition of MGDA-Na3 and solid MGDA-Na3.

In this process preferably the aqueous composition of MGDA-Na3 contains a higher amount of water than a crumbly phase composition, i.e. preferably more than 30 wt % of water on total aqueous composition. Even more preferably, the aqueous composition contains 35-60 wt % of MGDA-Na3.

It may be noted that EP0845456 also relates to a process of crystallizing a composition of MGDA-Na3 with a limited amount, namely 10-30%, of water. However as is clear from the Examples in this document, the starting composition employed in this document contains merely amorphous MGDA-Na3. To prepare a MGDA-Na3 solid of high crystalline content, mechanical stress is employed during the drying process. During crystallization a pasty, highly thixotropic, intermediate phase is formed. This gives rise to an increased chance on product quality fluctuations in case of process parameter fluctuations. It also seriously enhances the chance on full blockage of the process line, especially in case of power interruptions and the formation of a MGDA-Na3 solid product that is one clump, in the worst case of a concrete-like or gum-like texture that cannot be granulated anymore after it has been dried by commonly available mechanical granulation means such as a mill.

The present invention, identifying and exploiting a phase other than the paste phase, in which the composition shows granular flow behavior, avoids the problems that are related to the process described in EP0845456 and will effectively yield crystalline MGDA-Na3 product. Also, when preparing the crumbly phase composition of the present invention by adding a solution of MGDA-Na3 to solid MGDA-Na3 product, in preferred embodiments solid MGDA-Na3 product as obtained by drying a previous amount of crumbly phase composition, the pasty phase is altogether avoided, which ensures that measures to deal with thixotropic behavior can be avoided.

The present invention also provides a process to prepare MGDA-Na3 crystals comprising a step of drying the crumbly phase composition.

Using the process of the present invention wherein the above crumbly phase composition is subjected to a drying step, surprisingly a MGDA-Na3 crystalline product is obtained that has a high crystallinity, high bulk density, with predominantly or only close to spheroidal shaped particles having the particle size as requested by e.g. the detergent industry which is one of the main outlets for MGDA-Na3. The crystalline product as obtained was determined to consist for the major part of a particular crystal type, such as crystal type I if the crumbly phase product employed in preparing it also contains predominantly this same crystal type, such as the favored type I. The crystalline product remains free flowing at 70% relative humidity (RH) and 40° C. for at least 144 hours.

In addition, the process is a highly efficient process characterized by a high yield of high-quality product and no waste streams.

Finally, the present invention provides the product obtainable by the drying process. In embodiments, the drying process delivers solid crystalline MGDA-Na3 product that contains between 50 and 80% of the L enantiomeric form of MGDA (and hence 20-50% of the D enantiomeric form of MGDA) and that contains 90-99% MGDA-Na3 of crystal type I and 1-10% MGDA-Na3 of crystal type III on the basis of the total amount of MGDA-Na3 crystals in the MGDA-Na3 product.

Preferably, the solid crystalline MGDA-Na3 product obtainable by the drying process has a crystallinity between 60 and 100%, more preferably between 70 and 100%, most preferably between 75 and 100%.

In another preferred embodiment the MGDA-Na3 crumbly phase composition and solid crystalline MGDA-Na3 product obtainable by the drying process contains less than 0.01 wt % particulate solid with a pore volume in the range of from 0.25 to 0.75 cm$^3$/g, determined by nitrogen adsorption in accordance with 66134:1998-02 on total MGDA-Na3 weight.

In yet another preferred embodiment the crumbly phase composition contains crystal type I, or at least 75% of the crystalline MGDA-Na3 in the crumbly phase composition is of crystal type I, more preferably at least 90%.

In yet another preferred embodiment the solid crystalline MGDA-Na3 product obtainable by the drying process contains 92-97% MGDA-Na3 of crystal type I and 3-8% MGDA-Na3 of crystal type III on the basis of the total amount of MGDA-Na3 crystals in the product.

In yet another preferred embodiment the MGDA-Na3 crumbly phase composition contains between 20 and 30 wt % of water, more preferred between 21 and 27 wt % of water, most preferred between 22 and 26 wt % of water, the wt % being based on the total weight of the crumbly phase composition.

The weight percentage of organic compounds and salts thereof in the crumbly phase composition is in a preferred embodiment between 70 and 80 wt %, more preferred between 73 and 79 wt %, most preferred between 75 and 78 wt %, the wt % being based on the total weight of the crumbly phase composition.

Of the organic compounds and salts thereof as said at least 85 wt % is MGDA-Na3. Preferably at least 90 wt % of the organic compounds and salts thereof is MGDA-Na3. Other organic compounds and salts thereof that may be present include compounds that can be found in MGDA as remainders of the production process due to e.g. incomplete reaction of starting materials, side products, or compounds that are purposely added as an additive and include compounds such as citric acid or citrate salts, glycolic acid or glycolate salts, NTA-Na3, formic acid or formate salts, wherein NTA-Na3 stands for the trisodium salt of nitrilotriacetic acid.

In the water fraction in the crumbly phase a small amount of inorganic salts can be present. Such salts may be sodium hydroxide, sodium chloride, sodium silicate or sodium carbonate.

In a preferred embodiment the particles to make the crumbly phase have a particle size of smaller than 1.5 mm, even more preferably between 0.1-1.25 mm. In another preferred embodiment they have a crystallinity of at least 60%, more preferred at least 70%, most preferred at least 75% and up to and including 100%. The particles in an embodiment contain crystal type I, or at least 75% of the crystalline MGDA-Na3 in the particles is of crystal type I, more preferably at least 90%.

In another preferred embodiment the MGDA-Na3 in the crumbly phase composition is at least 70% crystalline, even more preferably at least 75%.

The MGDA-Na3 in the crumbly phase may be of the L enantiomeric form or of the D enantiomeric form. Preferably, the MGDA-Na3 is 50-100% in the L enantiomeric form (and thus 0-50% in the D enantiomeric form). Even more preferably the MGDA-Na3 is 50-80% in the L enantiomeric form, most preferably 50-65% in the L enantiomeric form.

The solid crystalline MGDA-Na3 product obtainable by the drying process in a preferred embodiment also is 50-100% in the L enantiomeric form (and thus 0-50% in the D enantiomeric form), even more preferably 50-80% in the L enantiomeric form, most preferably 50-65% in the L enantiomeric form.

It should be noted that the above three crystal types I, II and III have been primarily observed for MGDA-Na3 wherein there is a detectable amount of D enantiomer.

Preferably the aqueous composition that is used to prepare the crumbly phase contains 35-60 wt % MGDA-Na3, more preferably 40 to 60 wt % MGDA-Na3.

In an embodiment the process to dry the crumbly phase composition involves as a drying step a step selected from the group of an evaporation step, a step of fluid bed drying, a step of spray drying, a step of thin film drying, and, a step of drum drying, and a spray granulation step. The crumbly phase composition is in particular efficiently dried by simple drying processes such as drying processes that are based on simply evaporating free water such as in an oven, in a rotating evaporator, a drum a thin film drier, or on a moving belt or a fluid bed. When such processes involve a step in which the dry MGDA-Na3 is subjected to some mechanical energy, like in a fluid bed, a rotating drum, or on a moving belt, the product is immediately available in granules, when the drying step is done in the absence of mechanical energy such as in an oven, the product is obtained as a porous cake of solid crystalline material which has been found to be extremely easily granulated.

In the drying process a part of the crystalline product as obtained can be recycled and mixed with an aqueous solution containing MGDA-Na3 in an amount to prepare additional crumbly phase composition that subsequently is subjected to the drying process.

The drying step in a preferred embodiment is performed for a residence time of 1 minute to 5 hours if performed in an oven. When the drying step is done using a fluid bed, a thin film drier, a drum dryer or a moving belt, the drying step is preferably performed for a time of between 10 seconds and 30 minutes, even more preferably between 30 seconds and 15 minutes.

The drying step in another preferred embodiment is performed at a temperature of between 3° and 300° C. When an oven is used the temperature is more preferably between 4° and 100° C., while using a fluid bed, a drum or another rotating evaporator, or a moving belt the drying temperature is in more preferred embodiments between 7° and 200° C.

The drying process may be done as a batch process, semi continuous or continuous process. Preferably the process is performed continuously.

To identify the crystal type varieties and to determine the crystallinity, diffractograms were recorded using a Bruker-AXS D8 reflection-diffractometer with Ni filtered Cu-Kα radiation. Generator settings are 40 kV, 40 mA. Fixed sample irradiation 15 mm, Soller slits 2.5°. Measuring range: 2θ=5.0-70.0°, step size 0.02°, time per step 0.25 seconds.

The degree of crystallinity was ascertained from the X-ray powder diffractograms by determining the surface fraction of the crystalline phase and of the amorphous phase and using these to calculate the degree of crystallinity (also called "crystallinity"), as the ratio of the area of the crystalline phase, Ic, to the total area, consisting of the area of the amorphous phase, Ia, and the area of the crystalline phase, crystallinity (%): Ic/(Ic+Ia)*100.

This procedure was performed using Bruker EVA v.4.2.1.10 software with the following parameters: enhancement disabled, curvature 1, threshold 1.

Where in this document is referred to "free-flowability", this property was judged qualitatively by the following method About 4 gram of the materials were weighted into a crystallization dish (10 cm diameter) and evenly distributed over the bottom and subsequently stored in in a calibrated 70% RH climate chamber at 40° C. (Weiss SB11 500)

After storage the dish was tilted about 60° and gently tapped.

When all material falls to one side the material is judged "free flowing";

when a significant part of the material remains sticking on the bottom of the dish, the material is judged "partly free flowing";

when all material is stuck to each other the material is judged "caked".

A fourth option is that the material is partly up to fully "dissolved"; initially to be recognized by the appearance of a liquid phase, either in the form of tiny droplets on the glass walls or a glassy shiny layer upon the particle bed.

Bulk density was determined as freely settled bulk density.

The invention is illustrated by the examples below

EXAMPLES

Example 1 (Comparative)

A 50 wt % MGDA-Na3 aqueous slurry was prepared by crystallization evaporation, using MGDA-Na3 seeds of the type I variety. The slurry obtained was concentrated further using a laboratory rotary evaporator (temperature 50° C., pressure 200 mbar). At a concentration of 63 wt %, the slurry transformed into a pasty phase, yielding a sticky film on the wall of flask. Further drying yielded a hard film on the wall that could not be harvested efficiently anymore.

Example 2 (Comparative)

77 kg of a 40.7 wt % MGDA-Na3 aqueous solution was charged to a 80 L Vrieco-Nauta conical screw mixer. The solution was concentrated to 50 wt % MGDA-Na3 (jacket temperature: 50-120° C., pressure 100-200 mbar, screw speed 70 rpm). After adding 300 grams of MGDA-Na3 seeds of the type I variety, the slurry obtained was concentrated further. In the range of 60-65 wt % MGDA-Na3 a thixotropic pasty phase was formed, yielding serious fouling problems. The product eventually obtained was one large spheroidal lump of material that could not be processed further.

Example 3

A crumbly phase composition was prepared by first dosing 17.1 kg of solid MGDA-Na3 (particle size 0.1-1.25 mm), containing solely the type I crystal variety (MGDA-Na3 content 80.8 wt %, crystallinity 75%) to a 50 L Lödige Ploughshare mixer, operated at a rotation speed of 170 rpm, and subsequently dosing 2.9 kg of a 40.7 wt % MGDA-Na3 aqueous solution, during 5 minutes via a dosing pipe. The temperature during mixing was 30-40° C. After dosing, the product (MGDA-Na3 content: 75 wt %) was homogenized for 2 more minutes, before discharging the crumbly phase product.

Example 4

50 gram of the crumbly phase as obtained in example 3 was dried in petri-dish overnight in an oven at 90° C. The product obtained showing a MGDA-Na3 content of 81.3 wt %, was slightly caked, but could be easily crumbled, by gently tapping on the cake with a spatula, yielding free flowing particles in the range of 0.5-5 mm. The crystallinity of the product was 80%, showing solely the type I variety.

Example 5

500 gram of the crumbly phase as obtained in example 3 was dried using a laboratory rotary evaporator (temperature 80° C., pressure 500 mbar), during 30 minutes. The product obtained showing an MGDA-Na3 content of 82.1 wt %, was a free-flowing powder containing particles in the range of 0.5-3 mm. The crystallinity of the product was 77%, showing predominantly the type I variety and a small amount of a few percent of the type III variety.

Example 6

13 kg of the crumbly phase as obtained in example 3 was dried in a 16 L fluid bed drier, during 8 minutes (air temperature 150° C.; product end temperature 90° C.). Subsequently the product was milled using an Alexanderwerk friction sieve.

A free-flowing product was obtained showing an MGDA-Na3 content of 80.1 wt %. The crystallinity of the product was 79%, showing solely the type I variety 73 wt % of the product showed a particle size in between 0.5 and 1.5 mm. The bulk density was 850 Kg/m$^3$.

Visual inspection using a microscope showed that the majority of the particles had a spheroidal shape (potato-alike).

Example 7

A crumbly phase composition was prepared by first dosing 16 kg of solid MGDA-Na3 (particle size 0.1-1.25 mm), containing solely the type I crystal variety (MGDA-Na3 content 80.3 wt %, crystallinity 79%) to a 50 L Lödige Ploughshare mixer, operated at a rotation speed of 170 rpm, and subsequently dosing 2.55 kg of a 45.1 wt % MGDA-Na3 aqueous solution, during 5 minutes via a dosing pipe. The temperature during mixing was 45-50° C. After dosing, the product (MGDA-Na3 content: 76.1 wt %) was homogenized for 2 more minutes, before discharging the crumbly phase product.

The crumbly phase obtained was subsequently processed as described in example 6, yielding a free-flowing product showing an MGDA-Na3 content of 80.3 wt %. The crystallinity of the product was 78%, showing solely the type I variety. 68 wt % of the product showed a particle size in between 0.5 and 1.5 mm. The bulk density was 840 Kg/m$^3$.

What is claimed is:

1. A crumbly phase composition containing on total weight of the composition
   (i) 70-87 wt % of organic compounds and salts thereof containing 85 to 100 wt % of MGDA-Na3 on the basis of total organic compounds and salts thereof, wherein at least 60 wt % of the MGDA-Na3 is crystalline wherein the MGDA-Na3 that is crystalline is at least 75% of crystal type I on the basis of total crystalline MGDA-Na3 content, further wherein said crystal type I is a dihydrate crystal, and (ii) 20-30 wt % of water.

2. The crumbly phase composition of claim 1 containing on total weight of the composition
    (i) 70-80 wt % of organic compounds and salts thereof containing 85 to 100 wt % of MGDA-Na3 on the basis of total organic compounds and salts thereof.

3. The crumbly phase composition of claim 1 containing 75-80 wt % of organic compounds and salts thereof on the basis of the total weight of the composition.

4. The crumbly phase composition of claim 1 wherein the organic compounds and salts thereof contain more than 90 wt % of MGDA-Na3 on the basis of total organic compounds.

5. The crumbly phase composition of claim 1 containing between 50 and 80% of the L enantiomeric form of MGDA and between 20 and 50% of the D enantiomeric form of MGDA.

6. The process to prepare the crumbly phase composition of claim 1 comprising combining an aqueous composition of MGDA-Na3 and solid MGDA-Na3.

7. The process of claim 6 wherein the aqueous composition contains 35-60 wt % of MGDA-Na3.

8. The process to prepare solid crystalline MGDA-Na3 comprising a step of drying the crumbly phase composition of claim 1.

9. The process of claim 8 wherein the solid crystalline MGDA-Na3 contains 90-100% of crystal type I on total crystal content of MGDA-Na3.

10. The process of claim 8 wherein the process involves as a drying step a step selected from the group of an evaporation step, a step of fluid bed drying, a step of spray drying, a step of thin film drying, a step of drum drying, and a spray granulation step.

11. The process of claim 8 wherein in the process a part of the crystalline product as obtained is recycled and mixed with an aqueous composition containing MGDA-Na3 in an amount to prepare additional crumbly phase composition.

12. The process of claim 8 wherein the process is performed continuously.

13. The crumbly phase composition of claim 1 wherein the MGDA-Na$_3$ that is crystalline is at least 90% of crystal type I on the basis of total crystalline MGDA-Na$_3$ content.

14. The crumbly phase composition of claim 13 wherein the crystal type I has the following diffraction pattern:

| Type I | |
|---|---|
| 2Θ | d (Å) |
| 8.2 | 10.8 |
| 10.5 | 8.4 |
| 15.6 | 5.7 |
| 16.5 | 5.4 |
| 17.1 | 5.2 |
| 18.1 | 4.9 |
| 18.8 | 4.7 |
| 21 | 4.25 |
| 21.4 | 4.15 |
| 22.6 | 3.9 |
| 23.7 | 3.75 |
| 24.7 | 3.6 | wherein from 75 to 100 wt % of the MGDA-Na$_3$ is crystalline, wherein the water is present in an amount of from 22 to 26 wt %; and wherein the organic compounds and salts thereof are present in an amount of from 75 to 78 wt %.

15. The crumbly phase composition of claim 14 wherein 92 to 97% of the MGDA-Na$_3$ is of crystal type I on the basis of total crystalline MGDA-Na$_3$ content and 3 to 8% of the MGDA-Na$_3$ is of crystal type III on the basis of total crystalline MGDA-Na$_3$ content and has the following diffraction pattern:

| Type III | |
|---|---|
| 2Θ | d (Å) |
| 5.8 | 15.2 |
| 7.5 | 11.8 |
| 8.1 | 10.9 |
| 9.5 | 9.3 |
| 11.7 | 7.6 |
| 13.9 | 6.4 |
| 15.1 | 5.9 |
| 16.5 | 5.4 |
| 17.3 | 5.1 |
| 18.5 | 4.8 |
| 19.1 | 4.65 |
| 20.1 | 4.4 |

16. The crumbly phase composition of claim 15 containing between 50 and 80% of the L enantiomeric form of MGDA and between 20 and 50% of the D enantiomeric form of MGDA.

17. The crumbly phase composition of claim 16 that contains less than 0.01 wt % particulate solid with a pore volume in the range of from 0.25 to 0.75 cm$^3$/g, determined by nitrogen adsorption in accordance with 66134:1998-02 on total MGDA-Na$_3$ weight.

18. The crumbly phase composition of claim 1 wherein the MGDA-Na$_3$ that is crystalline is about 100% of crystal type I on the basis of total crystalline MGDA-Na$_3$ content.

* * * * *